US008638358B2

(12) United States Patent
Dabiri et al.

(10) Patent No.: US 8,638,358 B2
(45) Date of Patent: Jan. 28, 2014

(54) COLOR-CODED BACKLIGHTED SINGLE CAMERA THREE-DIMENSIONAL DEFOCUSING PARTICLE IMAGE VELOCIMETRY SYSTEM

(75) Inventors: Dana Dabiri, Brier, WA (US); Wei-Hsin Tien, Seattle, WA (US); Patrick Kartes, Charlotte, NC (US); Toru Yamasaki, Osaka (JP)

(73) Assignee: University of Washington, Seattle, WA (US)

( * ) Notice: Subject to any disclaimer, the term of this patent is extended or adjusted under 35 U.S.C. 154(b) by 753 days.

(21) Appl. No.: 12/727,167

(22) Filed: Mar. 18, 2010

(65) Prior Publication Data
US 2011/0025826 A1 Feb. 3, 2011

Related U.S. Application Data (63) Continuation of application No. PCT/US2008/076562, filed on Sep. 16, 2008.

(60) Provisional application No. 60/973,331, filed on Sep. 18, 2007.

(51) Int. Cl.
  *H04N 13/02* (2006.01)
(52) U.S. Cl.
  USPC ........ 348/47; 348/207.99; 348/266; 348/335; 356/28; 250/573; 250/208.1
(58) Field of Classification Search
  USPC ................ 348/47, 207.99, 266, 335; 356/28; 250/208.1, 363.6
  See application file for complete search history.

(56) References Cited

U.S. PATENT DOCUMENTS

| 4,988,190 A | 1/1991 | Miles |
| 6,507,391 B2 | 1/2003 | Riley |
| 7,006,132 B2 * | 2/2006 | Pereira et al. .............. 348/218.1 |
| 7,777,199 B2 * | 8/2010 | Madhavan et al. ......... 250/458.1 |

(Continued)

FOREIGN PATENT DOCUMENTS

KR 10-0518454 B1 9/2005

OTHER PUBLICATIONS

International Search Report with Written Opinion of the International Searching Authority mailed Jan. 29, 2009, issued in corresponding International Application No. PCT/US2008/076562, filed Sep. 16, 2008.

(Continued)

*Primary Examiner* — Christopher S Kelley
*Assistant Examiner* — Maria Vazquez Colon
(74) *Attorney, Agent, or Firm* — Christensen O'Connor Johnson Kindness PLLC (57) ABSTRACT

Three-Dimensional Defocusing Particle Image Velocimetry (3DDPIV) allows for measurement of three-dimensional velocities within a volume. In the disclosed embodiment, a mask with a plurality of apertures is disposed with a lens between the test section and a color camera. The field-of-view is backlit and the test section is seeded with black particles. This configuration allows for a lower power light source as compared to conventional 3DDPIV. Color-coded particle images are formed on a white background, wherein each of the color images is generated from light that travels through the filters not blocked by the imaged particle, thereby producing a color image that is of a color different from the color of any of the filters. A color space linear transformation is used to allow for accurate identification of each pinhole exposure when the color filters' spectrum does not match those of the 3-CCD color camera.

20 Claims, 4 Drawing Sheets

(56) References Cited

U.S. PATENT DOCUMENTS

2006/0175561 A1* 8/2006 Estevadeordal et al. ...... 250/573
2007/0195162 A1 8/2007 Graff

OTHER PUBLICATIONS

International Preliminary Report on Patentability mailed Jan. 7, 2010, issued in corresponding International Application No. PCT/US2008/076562, filed Sep. 16, 2008.

Estevadeordal, J., and L Goss, "PIV With LED: Particle Shadow Velocimetry (PSV)," Proceedings of the 43rd AIAA Aerospace Sciences Meeting and Exhibit, Reno, Nev., Jan. 10-13, 2005, AIAA 2005-37, pp. 1-10.

Kajitani, L., and D. Dabiri, "A Full Three-Dimensional Characterization of Defocusing Digital Particle Image Velocimetry," Measurement Science and Technology 16:790-804, 2005.

\* cited by examiner

COLOR-CODED BACKLIGHTED SINGLE CAMERA THREE-DIMENSIONAL DEFOCUSING PARTICLE IMAGE VELOCIMETRY SYSTEM

CROSS-REFERENCES TO RELATED APPLICATIONS

This application is a continuation of International Application No. PCT/US2008/076562, filed Sep. 16, 2008, which claims the benefit of U.S. Provisional Application No. 60/973,331, filed Sep. 18, 2007. Each application is expressly incorporated herein by reference in its entirety.

STATEMENT OF GOVERNMENT LICENSE RIGHTS

This invention was made with Government support under Government Contract No. 5R01RR023190 awarded by the National Institutes of Health. The Government has certain rights in the invention.

BACKGROUND

Particle image velocimetry ("PIV"), including digital particle image velocimetry ("DPIV"), has become a widely used quantitative flow visualization technique in fluid mechanics research due to its ability to provide non-intrusive, highly resolved measurement of planar velocity fields. With the use of ever-advancing CCD cameras, digital data acquisition systems, and sophisticated algorithms, DPIV continues to evolve and flourish. One of the key advancements is the development of Three-Dimensional Defocusing Particle Image Velocimetry ("3DDPIV"), which allows for three-dimensional velocity measurements within a volume. First proposed and established by Willert and Gharib (Willert, C. E., and M. Gharib, "Three-Dimensional Particle Imaging With a Single Camera," *Exp. Fluids* 12:353-358, 1992), this technique uses the defocusing concept to obtain a particle's position in three dimensions. Using a three-lens/CCD setup and a cross-correlation algorithm on sequential images, Pereira et al. (Pereira, F., et al., "Defocusing Digital Particle Image Velocimetry: A 3-Component 3-Dimensional DPIV Measurement Technique. Application to Bubbly Flows," *Exp. Fluids* 29:S78-84, 2000) mapped the bubbly flow field about a propeller using this concept. An error analysis with an uncertainty test was also reported. A two-dimensional theoretical basis of the optical design and velocity estimation methodology, together with a multi-surface refraction correction scheme, is later reported in Pereira F., and M. Gharib, "Defocusing Digital Particle Image Velocimetry and the Three-Dimensional," 2002. Kajitani and Dabiri established a full three-dimensional characterization of the 3DDPIV system and its associated geometric uncertainty (Kajitani, L., and D. Dabiri, "A Full Three-Dimensional Characterization of Defocusing Digital Particle Image Velocimetry," *Meas. Sci. Technol.* 16:790-80, 2005). Yoon and Kim adapted the defocusing concept and applied it to a micro-scale channel flow over a backward-facing step and obtained a time-averaged flow field (Yoon, S. Y., and K. C. Kim, "3D Particle Position and 3D Velocity Field Measurement in a Microvolume Via the Defocusing Concept," *Meas. Sci. Technol.* 17:2897-2905, 2006). Since their microscope's lens had multiple elements, they could not directly use the 3DDPIV relations established by Kajitani and Dabiri, which were based on a single-element lens. They therefore developed a calibration-based method to determine the depth location. Pereira et al. proposed a calibration procedure to approximate the multi-element lens optical system to a single-element lens system model, thereby overcoming the difficulty of determining the depth location (Pereira, F., et al., "Microscale 3D Flow Mapping With mDDPIV," *Exp. Fluids* 42:589-599, 2007). They then applied the single-lens concept to image a micro-volume 3D flow of an evaporating water droplet.

Initial implementations of 3DDPIV require three separate, yet properly coordinated, imaging systems integrated as a single unit to overcome the identification problem of overlapping particle exposures. This configuration is designed to image a large volume of interest because separating the three pinhole apertures into three individual lens/CCD systems makes it possible to increase the pinhole separation without using a costly customized large lens. Using this three-camera 3DDPIV system to measure velocities within small-scale flow fields has two major difficulties. First, due to its size and complexity, this type of system is hard to setup and calibrate. Second, with the presence of the pinhole mask, a high intensity light source is required to adequately illuminate the flow, which can noticeably heat and evaporate the fluid, thereby affecting the flow.

Efforts to avoid such difficulties in measuring flows within small volumes eventually lead to the original single camera configuration proposed by Willert and Gharib in 1992, which has been used by Yoon and Kim (2006) and Pereira et al. (2007).

Figure 1:
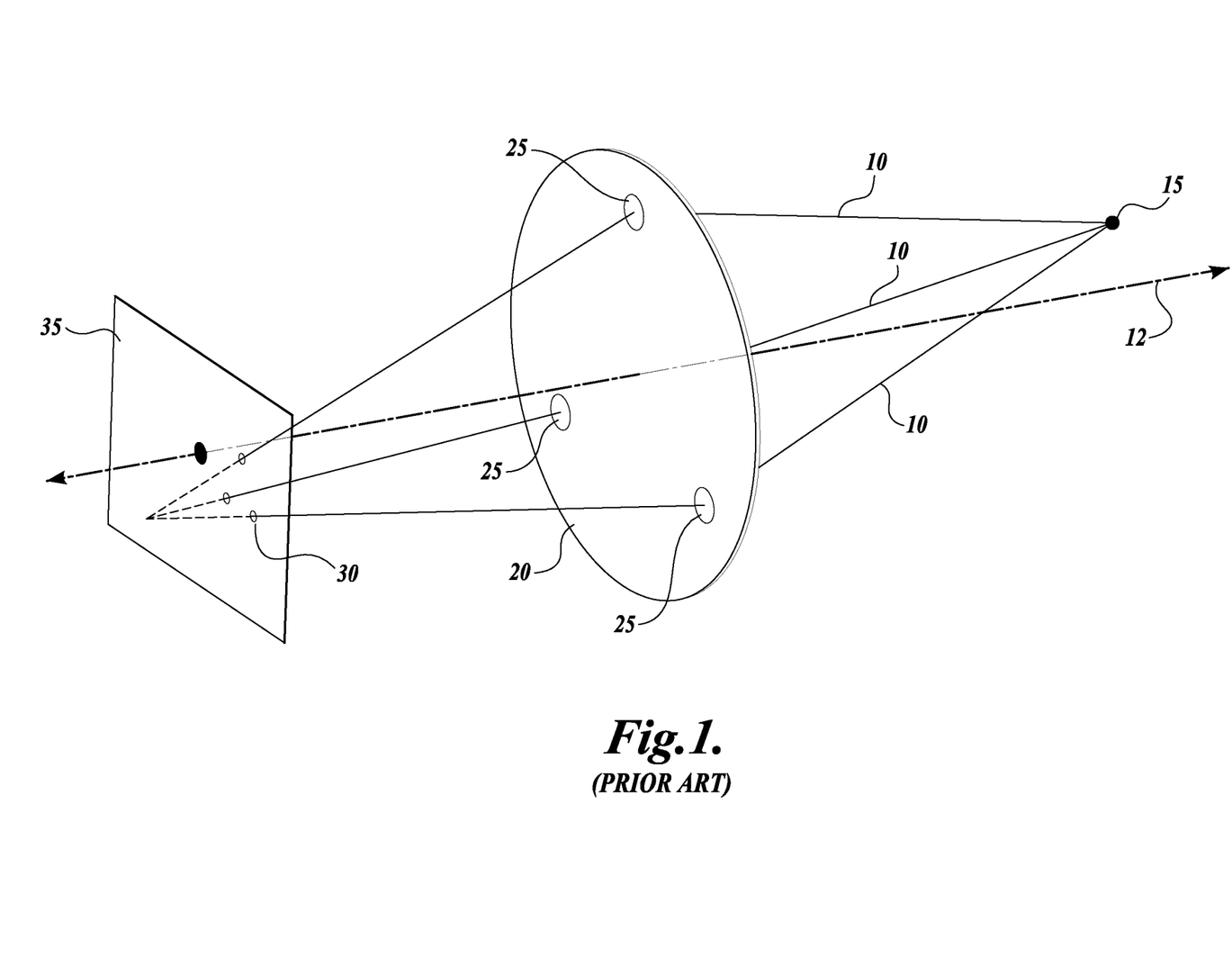
FIG. 1 is a diagram illustrating schematically a conventional 3DDPIV system.

The concept of the single camera 3DDPIV system is illustrated by a three-dimensional representation of the imaging system in FIG. 1 (Prior Art), which shows a particle 15 disposed on a fluid test region on one side of a lens place 20 having a mask defining three pinhole apertures 25. An imaging plane, or CCD plane 35, is disposed along the optical axis 12 opposite the test region. Light 10, reflecting from particles (e.g., particle 15) between the plane of focus (not shown, to the right of particle 15 in FIG. 1) and the lens plane 20 (the defocused region), passes through the pinholes 25 and forms triple exposures 30 (triplets) on the CCD plane 35. The size of the triplet depends on the location of the particle 15 within the defocused region. However, the system is difficult to use when the particle density becomes large due to overlapping triplet exposures, because the triplets become difficult to identify, separate, and use for particle identification. Furthermore, the necessity of the pinholes 25 has the unfortunate consequence of severely reducing the amount of light that exposes the CCD. Thus, a high intensity illumination source is needed.

There is a need, therefore, for a solution that overcomes the difficulties discussed above.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A color-coded backlighted single camera 3DDPIV system is developed to overcome the difficulties of the original single camera system. A pinhole mask with three color filtered pinholes is used to color-code each exposure of the defocused particle image, and a color splitting algorithm is developed to solve the particle identification problem. To overcome the limiting need for high intensity illumination for 3DDPIV systems, the modified system uses backlighting in conjunction with black particles. A calibration procedure to find the effective pinhole spacing was developed to give more accurate particle spatial coordinates, and a correction to the effective pinhole spacing for multi-surface refractions is also developed and validated by experiments. This technique is applied to a buoyancy-driven flow and a 3-D velocity field is successfully extracted.

While the color-coded backlighted single camera 3DDPIV system developed here has been demonstrated to be suitable for visualizing and quantifying micro-scale fluid flows, the use of backlighting, in conjunction with non-reflective particles can also be used to significantly reduce the illumination power requirements for multiple-CCD 3DDPIV systems. Furthermore, for higher speed flows, rather than using a continuous white light source, a pulsed white light source can be used to prevent particle image streaking.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

A system and method will now be described for conducting color-coded and backlighted 3DDPIV, with reference to the figures wherein like numbers indicate like elements. In 3DDPIV time-separated sequences of images of particles in the flow are used to determine the three-dimensional position of the particles, and the particle positions are tracked over time and used to determine the particle velocity.

Figure 2:
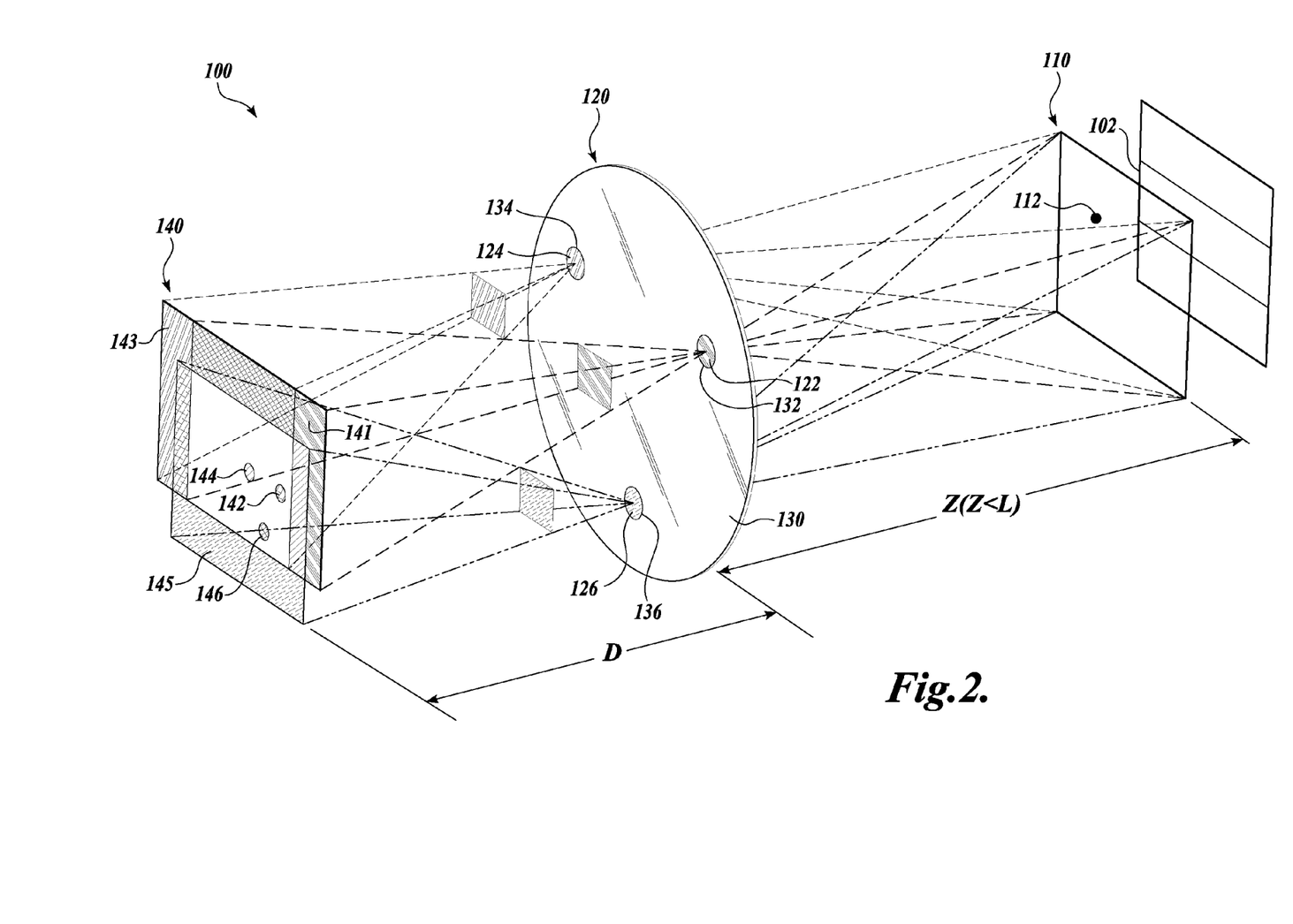
FIG. 2 is a diagram illustrating the basic operation of a color-coded backlighted single camera 3DDPIV system in accordance with the present invention.

Refer now to FIG. 2, which illustrates a simplified configuration for a 3DDPIV system 100 in accordance with the present invention. The system 100 includes a fluid test section (illustrated with a representative particle plane 110, for clarity), an image plane 140, a lens plane 120 defined by a lens with a pinhole mask 130, and a light source 102 positioned to backlight the test section. In a preferred embodiment the image plane 140 is defined by a color CCD camera, the lens plane 120 is defined by a lens (not shown) and the pinhole mask 130, and the light source 102 comprises a white light source such as a xenon flash lamp.

In this schematic a single particle 112 is shown in the particle plane 110 of the test section. In general the fluid test section will have a large plurality of particles suspended therein, and any particular plane is likely to intersect a plurality of particles, but for clarity in the following description the image generation for single particle 110 is shown.

The pinhole mask 130 is opaque, with a plurality of apertures that allow a portion of the light from the backlit test section to pass through the mask 130 and to the image plane 140. In this example, the mask 130 includes three pinhole apertures 132, 134 and 136 arranged in a triangular pattern. Those skilled in the art will appreciate that the number of apertures is exemplary only; a greater number of apertures may also be used.

Each of the apertures 132, 134, 136 has an associated color filter 122, 124, and 126. The filters 122, 124, 126 are different colors, and are preferably three primary colors, such as red, green, and blue. The filters 122, 124, 126 are preferably broadband filters and provide color-coded pinholes such that the light passing through the apertures 132, 134, 136 to the image plane 140 will produce a colored image at a color-capable camera such as a 3-CCD color camera. For simplicity, the following description assumes the three color filters 122, 124, and 126 are red, green, and blue, respectively. It will be appreciated that other color filters could alternatively be used. An important advantage is that the filters do not need to be narrow band optical filters.

FIG. 2 illustrates the image acquisition at the image plane 140. Light from the light source 102 passes through a viewable portion of the particle plane 110. A portion of the light passes through the lens and first filter 122 to produce a corresponding color image field 141 at the image plane 140. Because the test section is backlit, however, the particle 112 blocks some light from the first filter 122. Similarly, light from the light source 102 passes through the lens and second filter 124 to produce a second color image field 143 at the image plane 140, excepting the portion of light blocked by the particle 112. And, light from the light source 102 passes through the lens and third filter 126, producing a third color image field 145 at the image plane 140, excepting the portion of light blocked by the particle 112.

The three different color image fields 141, 143, 145 overlap at the image plane 140. Because the color filters 122, 124, 126 in this embodiment are primary colors, in superimposition they produce a white background. However, where only two color images overlap, they combine producing a corresponding color image.

In particular, where a portion of the light from one image field is blocked by the particle 112 at one of the three apertures, a color particle image results through the superposition of light coming through the remaining two apertures. Therefore, the light passing through the filters 122, 124, 126 in superposition produces a corresponding triplet of particle images 142, 144, and 146. This triplet of particle images 142, 144, and 146 is formed by the superimposition of light passing through the two apertures not blocked by the particle 112. Therefore, again assuming the color filters 122, 124, and 126 are red, green, and blue, respectively, the triplet of images 142, 144, and 146 will be cyan (green and blue), magenta (red and blue), and yellow (red and green), respectively.

When the test section includes a large plurality of particles, the projected triplet images 142, 144, 146 on the CCD plane 140 for a particular particle can be more easily determined because the triangular triplet images are color-coded. Furthermore, if the pinhole exposures for different particles overlap, the resulting color is also unique, still allowing for identification of each of the overlapped particles. In this manner, it is now possible to image high particle densities while eliminating the need for the more complex three-camera/lens system.

In the prior art 3DDPIV configuration shown in FIG. 1, light illuminates the seeding particle and the CCD camera images the light reflected from the particles. To suitably illuminate the particles for imaging in this manner requires a significant amount of light. Moreover, the mask with the pinhole apertures significantly reduces the amount of light reaching the CCD camera. Therefore, in such prior art systems a laser light source is typically used to provide sufficient reflected light. To overcome this difficulty, the system disclosed in FIG. 2 employs a backlighting method that does not rely on light reflected from the particles, and in fact optimally employs non-reflective seed particles.

Figure 3A:
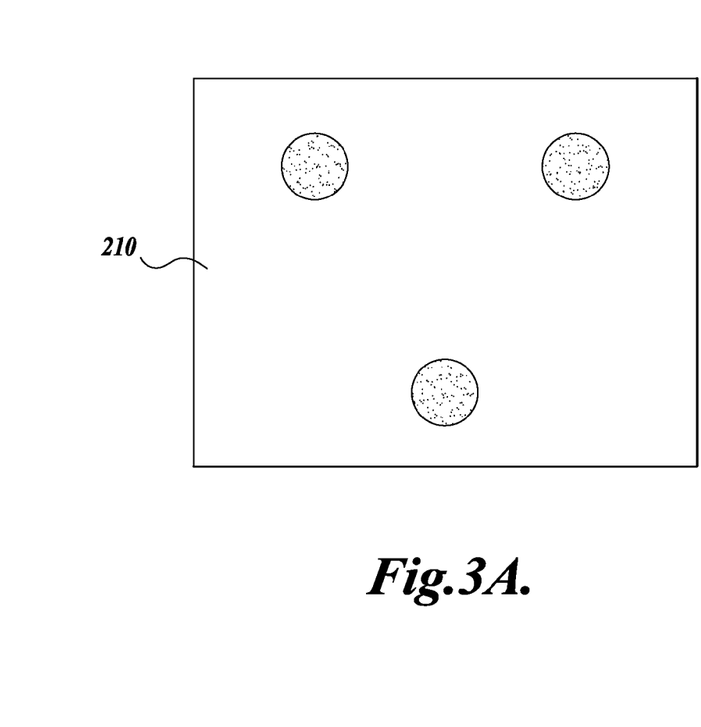
FIGS. 3A and 3B illustrate the resulting image on the CCD plane when no color filters are used (3A) and when color filters are used (3B) in combination with backlighting.
Figure 3B:
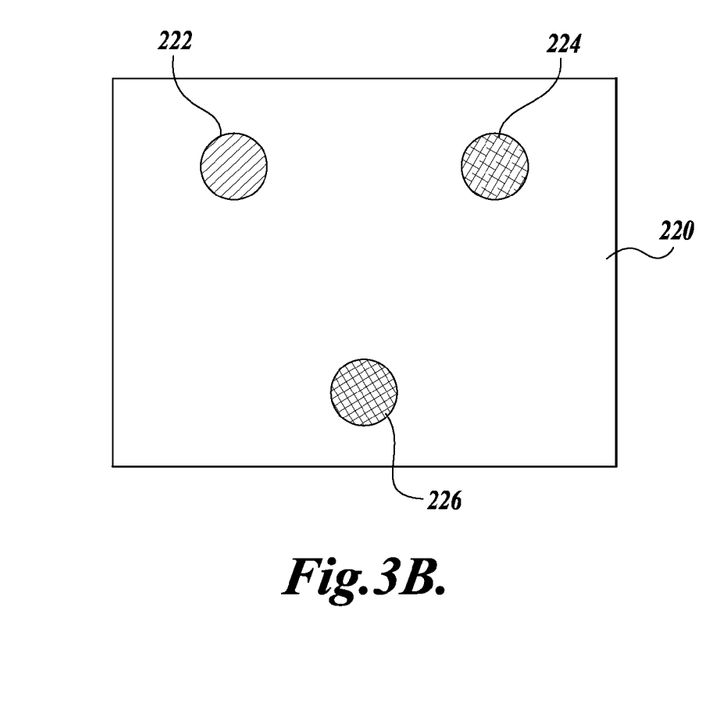

Therefore, in the preferred embodiment, the reflectivity of particle 112 is reduced, for example, by dyeing the particles black. The test section is then seeded with black, substantially non-reflective particles, such as the exemplary particle 112 shown in FIG. 2. It will be appreciated that the use of color filters 122, 124, and 126 to generate the images mitigates against the use of a single wavelength laser illumination source. Therefore, in the preferred embodiment the light source 102 comprises a white light source, such as a Xenon flash lamp. This light source 102 is oriented or adapted to illuminate directly towards the lens plane 120 and image plane 140 (i.e., the camera) resulting in an image with a white background and different colored triplet images, as discussed above. FIG. 3A shows the resulting triplet 210 if no color filters are used; FIG. 3B shows the resulting triplet 220 if the color filters, such as, for example, red, green, and blue color filters 122, 124, and 126 are used to cover the apertures, wherein particle image 222 is magenta, particle image 224 is cyan, and particle image 226 is yellow.

Identification of Defocused Particles by Color Separation

To identify the color-coded triplet images described above, a method for separating the three colors is necessary. In theory, this can be easily done if the spectrums of each of the red, green, and blue color filters perfectly match the spectrum of each of the red, green, and blue CCDs, respectively, since light emerging from each of the color filtered pinholes would expose only their respective CCDs. In reality, the spectrum of the broadband color filters and the CCDs do not match, thereby causing multiple pinhole exposures on each of the CCDs. A transformation algorithm defined by Pratt (Pratt, W. K., "Digital Image Processing," John Wiley & Sons, Inc., New York, N.Y., 1991) is therefore adopted to correct this problem.

The main concept of the transformation algorithm is to transform colors defined within an original set of primaries, $[P_1]$, $[P_2]$, and $[P_3]$, into another color space defined by a new set of primary colors $[P_1']$, $[P_2']$ and $[P_3']$. With this new set of primary colors, an arbitrary color, C, can be expressed by a new set of tristimulus values, $T'(C)$, that is based on the new set of primaries, $$T'(C) = \begin{bmatrix} T_1'(C) \\ T_2'(C) \\ T_3'(C) \end{bmatrix} \quad (1)$$

while the arbitrary color can also be expressed by the tristimulus values defined with the original primaries, $T(C)$, $$T(C) = \begin{bmatrix} T_1(C) \\ T_2(C) \\ T_3(C) \end{bmatrix} \quad (2)$$

Using the linear transformation of the primary colors' tristimulus values derived by Pratt (1991), the color matched by the original set of primaries (Red/Green/Blue or RGB), $T(C)$, can be transformed into the new set of primaries (Cyan/Magenta/Yellow or CMY), $T'(C)$, by the following equation:

$$\begin{bmatrix} T_1'(C) \\ T_2'(C) \\ T_3'(C) \end{bmatrix} = \begin{bmatrix} \begin{vmatrix} T_1(C) & T_1(P_2') & T_1(P_3') \\ T_2(C) & T_2(P_2') & T_2(P_3') \\ T_3(C) & T_3(P_2') & T_3(P_3') \end{vmatrix} / \begin{vmatrix} T_1(W) & T_1(P_2') & T_1(P_3') \\ T_2(W) & T_2(P_2') & T_2(P_3') \\ T_3(W) & T_3(P_2') & T_3(P_3') \end{vmatrix} \\ \begin{vmatrix} T_1(P_1') & T_1(C) & T_1(P_3') \\ T_2(P_1') & T_2(C) & T_2(P_3') \\ T_3(P_1') & T_3(C) & T_3(P_3') \end{vmatrix} / \begin{vmatrix} T_1(P_1') & T_1(W) & T_1(P_3') \\ T_2(P_1') & T_2(W) & T_2(P_3') \\ T_3(P_1') & T_3(W) & T_3(P_3') \end{vmatrix} \\ \begin{vmatrix} T_1(P_1') & T_1(P_2') & T_1(C) \\ T_2(P_1') & T_2(P_2') & T_2(C) \\ T_3(P_1') & T_3(P_2') & T_3(C) \end{vmatrix} / \begin{vmatrix} T_1(P_1') & T_1(P_2') & T_1(W) \\ T_2(P_1') & T_2(P_2') & T_2(W) \\ T_3(P_1') & T_3(P_2') & T_3(W) \end{vmatrix} \end{bmatrix} \quad (3)$$

where W represents the reference white color.

To find the new set of primaries, a black dot patterned transparency is put within the defocusing region, thereby generating triplets with cyan, magenta, and yellow dots imaged with the modified 3DDPIV camera system. To identify cyan, magenta, and yellow in terms of the original RGB primaries, the background is separated from the particles by using its low saturation as a thresholding criterion. For the remaining pixels, the RGB color space is converted into HSV in Matlab.

Once the CMY peaks are identified, they are re-transformed to the RGB domain, so that they can be used within equation (3) to identify colors defined by the new CMY primaries for all pixels within the image that do not have low saturation values. Application of this procedure easily allows for splitting the three CMY channels, where each channel represents the intensity image from each pinhole. While its intensity cannot provide useful information to identify each exposure, the color separation procedure clearly identifies overlapped particles.

Experimental Setup

Figure 4:
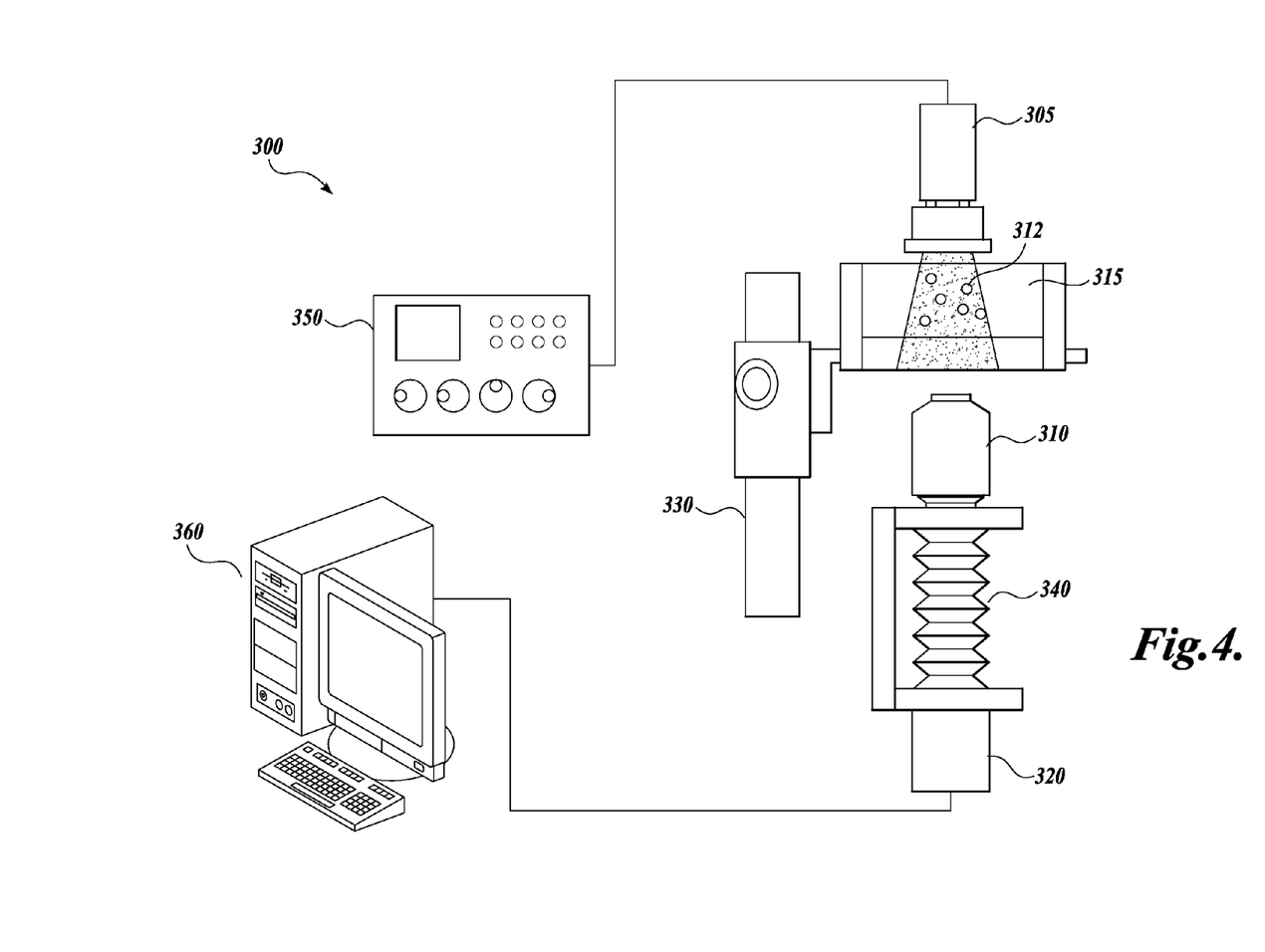
FIG. 4 is a diagram illustrating an apparatus for implementing the 3DDPIV illustrated in FIG. 2, using color filters, backlighting and a single camera for performing three-dimensional defocusing particle image velocimetry.

FIG. 4 illustrates the exemplary color-coded backlighted single camera 3DDPIV system setup used for performing three-dimensional defocusing particle image velocimetry. Those skilled in the art will appreciate that the parameters and the make of the system elements described below serve for illustrative purposes only and should not be construed as limiting.

The system 300 comprises a light source 305, in one embodiment a Xenon flash lamp; a camera lens 310, in one embodiment a Nikon AF Micro 105 mm; a pinhole mask with pinholes (not shown), preferably 2.74 mm diameter, that are located at the vertices of an equilateral triangle, preferably with side lengths of 15 mm; three color filters (not shown), in one embodiment Roscolux CalColor 90 Red #4690, CalColor 90 Green 4490, and Calcolor 90 Blue #4290; a 3-CCD chip camera 320, in one embodiment a 640×480 pixels Sony XC-007; and a translation stage 330. The three-pinhole mask with color filters is placed inside the lens 310. In one embodiment, the lens 310 may be attached to the camera 320 via a bellows tube 340 at a distance such that the measured magnification factor is approximately 2.69. The resulting imaging volume is 3.35×2.5×1.5 mm³.

The light source 305 is pulsed by pulse generator 350, in one embodiment at 15 Hz, and located sufficiently far from the lens 310 so the resulting white background is uniform. The particles 312 (not to scale) are dyed black to absorb incident light, and are used to seed the flow within the test section 315. In one embodiment, the particles 312 may have a twenty micrometer diameter and may be made of polystyrene.

The camera 320 is connected to a computer 360 that receives the triplet images captured by the camera 320 and may be used for image processing. It should be understood by those skilled in the art that other configurations and types of the system elements may also be used within the scope of the proposed system.

Calibration of the Particle Spatial Coordinates

The complete three-dimensional mapping relation between the spatial coordinates (X,Y,Z) and image coordinates (x,y) of each pinhole exposure image has been derived previously (Grothe, R., et al., "An Improved Three-Dimensional Characterization of Defocusing Digital Particle Image Velocimetry (DDPIV) Based on a New Imaging Volume Definition," *Meas. Sci. Technol.* 19:065402, 2008), which is hereby incorporated by reference in its entirety.

The spatial coordinates, X and Y, are functions of the average image coordinates, $x_0$ and $y_0$, magnification of the optical system, M, distance from the lens plane to the reference plane, L, and spatial coordinate, Z.

$$X = \frac{-x_0 Z}{ML}, \quad Y = \frac{-y_0 Z}{ML} \quad (4)$$

The spatial coordinate, Z, is also shown to be:

$$Z = \left(\frac{1}{L} + \frac{b}{MdL}\right)^{-1} \quad (5)$$

where b is the image separation and d is the distance between the pinhole apertures.

Since these derivations assumed that the system was comprised of a single-element lens, d has been a known parameter. However, since the present lens contains multiple elements, and since the pinhole mask is placed within the lens, an "effective" pinhole separation, d', should be used rather than the actual pinhole separation, d, in the above equations. This inconsistency is a source of error in the displacement measurements and will also reduce the precision of the velocity measurements. In addition, since the lens is multi-element, L is not readily known either. To solve these problems, a calibration procedure is developed to determine the "effective" pinhole separation, d,' as well as compensate for the unknown distance, L.

Particles placed on the bottom surface of the test section are first imaged at the focal plane, resulting in only single particle exposures. The test section is then moved towards the lens system by a distance $h_1$, causing defocused triple particle exposures with a separation distance $b_1$. The Z location of a particle on the bottom surface of the test section is then calculated using equation (5), where d is replaced by the "effective" pinhole separation d':

$$Z = \left(\frac{1}{L} + \frac{b}{Md'L}\right)^{-1} \quad (6)$$

Using the approach taken by Pereira et al. (Pereira, F., et al., "Microscale 3D Flow Mapping With mDDPIV," *Exp. Fluids* 42:589-599, 2007), Z can be represented by the displacement $h_1$ and L:

$$L - Z = h_1 \Rightarrow Z = L - h_1 \quad (7)$$

where L can be determined by the nominal magnification M and focal length of the lens f from the lens equation:

$$M = \frac{f}{L-f} \Rightarrow L = \frac{f(1+M)}{M} \quad (8)$$

Combining equations (6)-(8), the effective spacing of the pinhole apertures, d', can be calculated from the image separation $b_1$, magnification M, focal length of the camera f, and the displacement $h_1$:

$$d' = \frac{b_1}{M}\left(\frac{f(1+M)}{Mh_1} - 1\right) \quad (9)$$

Rewriting equation (9), and assuming f>>$h_1$, the relation of $b_1$ and $h_1$ can be written as:

$$b_1 = \frac{d'M^2 h_1}{f(1+M) - Mh_1} \approx \frac{d'M^2}{f(1+M)} h_1 \quad (10)$$

Repeating the procedure for different distances, $h_2$, $h_3$, . . . , a set of image separations, $b_2$, $b_3$, . . . , can be measured. Equation (10) suggests that the relation between the separation b and distance h should be accurately approximately by a straight line. Using a least square curve fit, the slope of the line can be found and d' can be determined given the focus length of the lens, f, and the magnification, M. The focus length f is a known parameter of the lens, and the magnification M is obtained by directly measuring an exact known length in physical space in the image. In this way, the system of equations used to describe 3DDPIV systems with a single-element lens can be used to describe 3DDPIV systems with a multi-element lens, thereby allowing for its methodology to determine three-dimensional velocities.

In practice, light passes through the fluid, the transparent container wall, and the air before entering the lens system. Therefore, the multiple refractions will change the path of the incident ray and make the measured Z location appear smaller than its actual location, Z', for the case without fluid in the test section. For the case with fluid in the test section, the fluid index of refraction is different from that of the glass plate, thus resulting in an actual location Z", different than Z'. Z" is usually larger than Z', because the fluid index of refraction (water, n"=1.333) is smaller than the glass plate's index of refraction (n'=1.5). The correction for the Z location due to such refractions is derived in Pereira and Gharib (2002) as follows:

$$Z'' = D + t + \left[Z - D - \frac{t}{\Omega(n')}\right] \times \Omega(n'') \quad (11)$$

with $\Omega(v) = \sqrt{\frac{R^2}{Z^2}\left[\left(\frac{v}{n}\right)^2 - 1\right] + \left(\frac{v}{n}\right)^2} \approx \sqrt{\left(\frac{v}{n}\right)^2} = \frac{v}{n}$ for $R = X^2 + Y^2$ and $R \ll Z$ where D is the distance from the lens plane to the bottom surface of the test section, t is the thickness of the bottom surface of the test section, and n, n' and n" are the indices of refraction of air, glass and fluid, respectively. The simplification shown in equation (11) is valid since in the present configuration R<5 mm and Z>140 mm Since the actual Z location is now Z", the depth, h, used in section 5.1 needs to be adjusted due to refractive effects through multiple surfaces to obtain a more accurate d'. For the case without fluid, the actual particle location Z', is calculated using the same equation (11), with n"=1, indicating the fluid is air.

To correct for d', L from equation (8) is substituted in equation (6), resulting in $$Z = \frac{f^2(1+M)d}{bf + dMf} \quad (12)$$

In equation (7), L and Z are replaced by their effective values, L" and Z", respectively, where $L"=Z"|_{b=0}$·h is also be replaced by its effective value, h"

$$h" = \frac{h}{\Omega(n")} = L - Z \quad (13)$$

resulting in the corrected effective d', d", $$d" = \frac{b_1}{M}\left(\frac{f(1+M)}{Mh"} - 1\right) \quad (14)$$

Similarly, assuming $f \gg h_1$, the relation of $b_1$ and $h_1$ can be written as:

$$b_1 = \frac{d"M^2 h_1"}{f(1+M) - Mh_1"} \approx \frac{d"M^2}{f(1+M)}h_1" \quad (15)$$

Equation (15) is similar to equation (10); however, the effective d' is replaced by d", which has a refraction correction effect due to the index refraction of the fluid, n". It is interesting that equation (15) shows that d" is not affected by the glass plate's index of refraction, and that the depth of the fluid does not affect Z" or d".

The increase in the length of the effective pinhole separation and the multi-surface refraction correction, also affect the sensitivity of the system. For a system without fluid, Willert and Gharib defined this sensitivity as the change of the triplet image size to the change of depth:

$$\frac{\partial b}{\partial Z} = -\frac{MdL}{Z^2} \quad (16)$$

where $$Z = \left(\frac{1}{L} + \frac{b}{MdL}\right) \quad (17)$$

Using d" instead of d' in equation 6, and using it to replace Z in equation (11), it can be shown that with multi-surface refraction corrections, the system sensitivity is:

$$\frac{\partial b}{\partial Z} = -\frac{Md"L}{Z^2}\frac{n}{n"} \quad (18)$$

It can be immediately seen that an increased effective pinhole separation increases the system sensitivity, while the index of refraction ratio will most often decreases the sensitivity, since in most applications, n corresponds to the refraction index of air, while n" corresponds to the refraction index of the fluid.

Images are captured by a frame grabber into a computer, and processed by a 4-stage image processing procedure to calculate the particle locations. Upon particle identification, triplets and velocities are determined via procedures that have been previously published (Pereira F., et al., "Defocusing Digital Particle Image Velocimetry: A 3-Component 3-Dimensional DPIV Measurement Technique. Application to Bubbly Flows," *Exp. Fluids* 29:S78-84, 2000).

In the first stage, the raw image is pre-processed to eliminate the background variation. The procedure is comprised of contrast enhancement and a Gaussian band-pass filter to reduce the high-frequency signal noise and the low-frequency bulk color variation of the background. The second stage separates the particle images within the triplets by separating the CMY colors. The third stage post-processes the images, where the background of each grayscale image is removed by thresholding. In the final stage, these particle images are analyzed to identify triplets, then particles locations in spatial coordinates, and finally the velocity field.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for performing three-dimensional defocusing particle image velocimetry comprising:
providing a test section comprising a transparent fluid having a substantially non-reflecting particle suspended therein;
providing a white light source disposed on one side of the test section;
providing a lens disposed on a side of the test section opposite the white light source, the lens including an opaque mask defining at least three apertures such that light from the white light source travels through the lens;
providing at least three color filters corresponding to the at least three apertures, each filter covering one aperture and each filter having a different color;
providing an image detecting element adapted to detect color images, the image detecting element receiving light transmitted through the lens, and arranged such that light from the white light source travels through the test section, then through the lens and color filters to generate at the image detecting element a set of color images corresponding to the suspended particle, each of the color images in the set being generated from light that travels through the filters not blocked by the suspended particle, thereby producing a color image that is of a color different from the color of any of the filters;
obtaining a first set of color images from the image detecting element at a first time and determining a first three-dimensional position of the particle based on the first set of color images;
obtaining a second set of color images from the image detecting element at a second time and determining a second three-dimensional position of the particle based on the second set of color images; and
calculating the velocity of the particle using the first and second sets of color images.

2. The method of claim 1, wherein the substantially non-reflective particle is colored black.

3. The method of claim 1, wherein the at least three apertures comprises three apertures.

4. The method of claim 1, wherein the light source comprises a flash lamp.

5. The method of claim 1, wherein the mask is affixed directly to the lens.

6. The method of claim 1, wherein the image detecting element is selected from one of a single 3-CCD color camera and a single CCD color camera.

7. The method of claim 1, wherein the suspended particle comprises a polymeric foam particle having a diameter of not more than twenty micrometers.

8. The method of claim 1, wherein the filters are not narrow band optical filters.

9. The method of claim 3, wherein the color filters comprise a red filter, a green filter, and a blue filter.

10. The method of claim 1, wherein the white light source produces a white background on the image detecting element formed by a superposition of light traveling through the apertures of the opaque mask.

11. The method of claim 1, further comprising the step of identifying the color images corresponding to the particle using a color separation technique.

12. A system for performing three-dimensional defocusing particle image velocimetry, the system comprising:
a test section comprising a transparent fluid having a plurality of substantially non-reflecting particles suspended therein;
a white light source disposed on a first side of the test section;
a lens disposed on a second side of the test section opposite the first side, the lens including an opaque mask defining at least three apertures and positioned to admit light from the white light source through the apertures;
at least three color filters corresponding to the at least three apertures, each color filter covering one aperture, each filter having a different color;
an image detecting element adapted to detect color images, the image detecting element configured to receive light transmitted through the lens;
wherein light from the white light source travels through the test section, then through the color filters and the lens to generate a set of color images on the image detecting element for each of the plurality of particles, wherein each image in the set of color images is generated from light that travels through the filters not blocked by the suspended particle such that the image is of a color different from the color of any of the filters.

13. The system of claim 12, wherein the substantially non-reflective particles comprise foam particles that are colored black.

14. The system of claim 12, wherein the at least three apertures comprise exactly three apertures.

15. The system of claim 12, wherein the light source comprises a flash lamp.

16. The system of claim 12, wherein the mask is affixed directly to the lens.

17. The system of claim 12, wherein the image detecting element is selected from one of a single 3-CCD color camera and a single CCD color camera.

18. The system of claim 12, wherein each particle has a diameter of not more than twenty micrometers.

19. The system of claim 12, wherein the at least three color filters comprise a red filter, a green filter, and a blue filter.

20. The system of claim 12, wherein each of the detected colored images comprise shadows formed by the particles blocking one of the apertures and a superposition of light emerging through the remaining apertures.

* * * * *